United States Patent [19]

Durant et al.

[11] 4,080,459

[45] Mar. 21, 1978

[54] PYRIDYL-ALKYLAMINOETHYLENE COMPOUNDS

[75] Inventors: Graham John Durant, Welwyn Garden City; John Colin Emmett, Codicote; Charon Robin Ganellin, Welwyn Garden City; Hunter Douglas Prain, Welwyn, all of England

[73] Assignee: Smith Kline & French Laboratories Limited, Welwyn Garden City, England

[21] Appl. No.: 743,446

[22] Filed: Nov. 19, 1976

Related U.S. Application Data

[60] Division of Ser. No. 629,194, Nov. 5, 1975, Pat. No. 4,013,769, which is a continuation-in-part of Ser. No. 468,617, May 9, 1974, Pat. No. 3,953,460.

[51] Int. Cl.$^2$ .................... A61K 31/44; C07D 213/28
[52] U.S. Cl. ........................... 424/263; 260/294.8 D; 260/294.8 F; 260/294.8 G; 260/294.9

[58] Field of Search ................. 260/294.8 F, 294.8 D, 260/294.9, 294.8 G; 424/263

[56] References Cited

U.S. PATENT DOCUMENTS

| 3,734,924 | 5/1973 | Black et al. | 424/263 |
| 3,736,331 | 5/1973 | Black et al. | 424/263 |
| 3,759,944 | 9/1973 | Black et al. | 424/263 |
| 3,894,151 | 7/1975 | Black et al. | 424/263 |

Primary Examiner—Alan L. Rotman
Attorney, Agent, or Firm—Joan S. Keps; Richard D. Foggio; William H. Edgerton

[57] ABSTRACT

The compounds are ethylene derivatives which are inhibitors of histamine activity, in particular, inhibitors of H-2 histamine receptors. A compound of this invention is 1-nitro-2-[2-((4-methyl-5-imidazolyl)methylthio)ethylamino]2-[2-((3-chloro-2-pyridyl)methylthio)ethylamino]ethylene.

9 Claims, No Drawings

PYRIDYL-ALKYLAMINOETHYLENE COMPOUNDS

This is a division of application Ser. No. 629,194 filed Nov. 5, 1975, now U.S. Pat. No. 4,013,769, dated Mar. 22, 1977, which is a continuation-in-part of Ser. No. 468,617 filed May 9, 1974, now U.S. Pat. No. 3,953,460, dated Apr. 27, 1976.

This invention relates to ethylene derivatives, in particular to pharmacologically active 1,1-diaminoethylene derivatives. These compounds are inhibitors of H-2 histamine receptors. In addition, this invention relates to pharmaceutical compositions comprising these compounds and to methods of inhibiting H-2 histamine receptors with these compounds. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has been described by Black et al. (Nature 1972, 236, 385) which are distinguished by the fact that they act at histamine receptors other than the H-1 receptor and these other receptors have been designated at H-2 receptors. This latter group of substances, to certain of which the present invention relates, are thus of utility in inhibiting certain actions of histamine which are not inhibited by the above-mentioned "antihistamines", that is they are H-2 histamine receptor inhibitors. Inhibitors of H-2 histamine receptors are useful, for example, as inhibitors of gastric acid secretion. The substances of this invention may also be of utility as inhibitors of certain actions of gastrin.

In the treatment of certain conditions, for example inflammation, and in inhibiting the actions of histamine on blood pressure, combination of H-1 and H-2 receptor inhibitors is useful.

The 1,1-diaminoethylene derivatives with which the present invention is concerned may be represented by the following general formula:

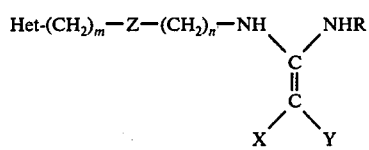

wherein X and Y, which may be the same or different, are hydrogen, nitro, cyano or $SO_2Ar$ but are not both hydrogen or both nitro; R is $Het'(CH_2)_{m_1}Z'(CH_2)_{n_1}$; Z and Z' are sulphur or methylene; $m$ and $m_1$ are 0, 1 or 2 and $n$ and $n_1$ are 2 or 3 provided that each of the sum of $m$ and $n$ and the sum of $m_1$ and $n_1$ is 3 or 4; Het is a pyridine ring which ring is optionally substituted by lower alkyl, hydroxyl, halogen or amino; Het' is a nitrogen containing 5 membered heterocyclic ring such as imidazole, oxazole, isoxazole, triazole, thiazole, isothiazole or thiadiazole which ring is optionally substituted by lower alkyl, hydroxyl, halogen or amino; and Ar is an aryl group such as phenyl optionally substituted by halogen or methyl or a pharmaceutically acceptable acid addition salt thereof.

It will be appreciated that $m_1$, $n_1$, and Z' in R need not have the identical significance as $m$, $n$ and Z in the other part of the formula.

Throughout the present specification by the term "lower alkyl" we mean an alkyl group containing from 1 to 4 carbon atoms.

It will be understood that the structure illustrated in Formula I and in Formula I(a) below, is only one of several representations and that other tautomeric forms as shown in Formulae II and III and the other geometrical isomer shown in Formula IV are also covered by the present invention. In Formulae II to IV and I(a) $R^1$ represents $Het-(CH_2)_m-Z(CH_2)_n$.

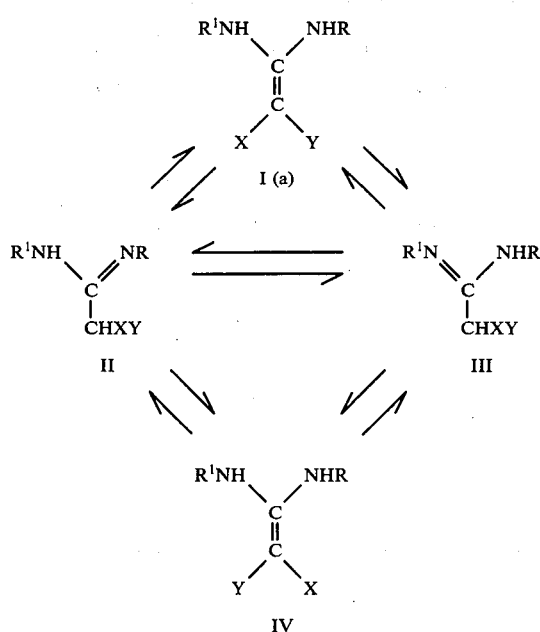

In a preferred group of compounds of Formula I, R is Het'—CH$_2$SCH$_2$CH$_2$, Z is sulphur, $m$ is 1 and $n$ is 2. Most suitably Het' is imidazole, thiazole or isothiazole and is optionally substituted by methyl or halogen.

It is also preferred that X should be nitro and Y should be hydrogen.

Particular compounds of this invention are: 1-nitro-2-[2-((4-methyl-5-imidazolyl)methylthio)ethylamino]-2-[2-((3-chloro-2-pyridyl)methylthio)ethylamino]ethylene and 1-nitro-2-[(2-thiazolylmethylthio)ethylamino]-2-[2-((3-chloro-2-pyridyl)methylthio)ethylamino]ethylene.

A general method for the preparation of the compounds of the present invention is shown in the following scheme 1.

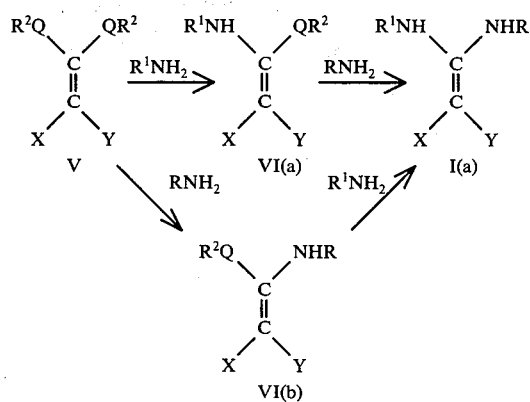

The starting material is a compound of Formula V wherein Q is sulphur or oxygen, preferably sulphur, and R$^2$ is lower alkyl such as methyl, or aralkyl, such as benzyl, but is preferably methyl. This may be reacted with one equivalent of R$^1$NH$_2$ or of RNH$_2$, R$^1$ and R have the same significance as in Formula I, to give respectively the compounds of Formulae VI(a) or VI(b) and then reacted with RNH$_2$ or R$^1$NH$_2$ respectively to give the compound of Formula I(a). The reactions described in Scheme 1 may be carried out in a suitable solvent or in the absence of a solvent at a moderately elevated temperature, for example at from 90°–150° C.

The intermediate of Formula V wherein Q is sulphur (see Formula V(a) in the following Scheme 2):

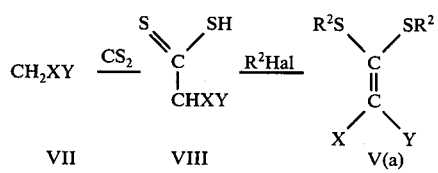

may be formed from the substituted methane of Formula VII by treatment of the latter with a strong base such as sodium hydride or sodium hydroxide and reaction with carbon disulphide to give the compound of Formula VIII. Treatment of this substance with an alkyl or aralkyl halide of Formula R$^2$ Hal gives the required compound of Formula V(a).

It will be appreciated that the final stage of the reactions shown in Scheme 1 may all be expressed by the following reaction:

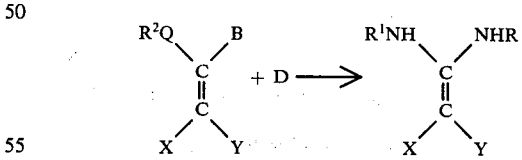

wherein B is RNH or R$^1$NH; D is R$^1$NH$_2$ or RNH$_2$; X, Y, R and R$^1$ have the same significance as in Formula I(a) and Q and R$^2$ have the same significance as in Formula V, provided that, when B is RNH, D must be R$^1$NH$_2$.

As stated above, the compounds represented by Formula I have been found to have pharmacological activity in the animal body as antagonists to certain actions of histamine which are not blocked by "antihistamines" such as mepyramine.

For example they have been found to inhibit selectively the histamine-stimulated secretion of gastric acid from the perfused stomachs of rats anaesthetised with urethane at doses of from 0.5 to 256 micromoles per kilogram intravenously. Similarly, the action of these compounds is demonstrated by their antagonism to the effects of histamine on other tissues which, according to the above-mentioned paper of Black et al., are H-2 receptors. Examples of such tissues are perfused isolated guinea-pig atrium and isolated rat uterus. The compounds of the invention have also been found to inhibit the secretion of gastric acid stimulated by pentagastrin or by food.

The level of activity found for the compounds of the present invention is illustrated by the effective dose range in the anaesthetised rat, as mentioned above of from 0.5 to 256 micromoles per kilogram, intravenously. Many of the compounds of the present invention produce a 50% inhibition in this test at a dose of from 1 to 10 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol.

Pharmaceutical compositions comprising a pharmaceutical carrier and a compound of Formula I or a pharmaceutically acceptable acid addition salt thereof and methods of inhibiting H-2 histamine receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 to about 250 mg, most preferably from about 100 to about 200 mg.

The active ingredient will preferably be administered in equal doses of one to three times per day. The daily dosage regimen will preferably be from about 150 to about 750 mg, most preferably from about 300 to about 600 mg.

Other pharmacologically active compounds may in certain cases be included in the composition. Advantageously the composition will be made up in a dosage unit form appropriate to the desired mode of administration, for example as a tablet, capsule or injectable solution. The invention is illustrated but in no way limited by the following examples:

EXAMPLE 1

1-Nitro-2-[2-(4-methyl-5-imidazolyl)methylthio)ethylamino]-2-[2-((3-bromo-2-pyridyl)methylthio)ethylamino]ethylene (a)(i) A solution of 4-methyl-5-[(2-aminoethyl)thiomethyl]-imidazole (1.71 g) in t-butanol (30 ml) was added slowly to a solution of 1-nitro-2,2-bis methylthioethylene (1.66 g) in acetonitrile (20 ml) at room temperature. The solution was heated under reflux for 3 hours, evaporated to dryness and chromatographed on a column of silica gel with elution by anhydrous ether (250 ml) followed by acetone (500 ml). The acetone eluate was concentrated to low bulk to give 1-nitro-2-methylthio-2-[2-((4-methyl-5-imidazolyl)methylthio)ethylamino]ethylene (1.58 g), m.p. 151°–153°. A sample recrystallised from acetonitrile had m.p. 152°–153°.

(Found: C, 41.4; H, 5.3; N, 19.4; S, 21.8; $C_{10}H_{16}N_4O_2S_2$ requires: C, 41.7; H, 5.6; N, 19.4; S, 22.2).

(ii) A mixture of 1-nitro-2-methylthio-2-[2-((4-methyl-5-imidazolyl)methylthio)ethylamino]ethylene (0.67 g) and 2-[(2-aminoethyl)thiomethyl]-3-bromopyridine (0.58 g) are mixed and heated together on a steam bath for 2 hours. Recrystallisation of the cooled melt furnishes the title product.

(b)(i) A solution of 2-[(2-aminoethyl)thiomethyl]-3-bromopyridine (from the dihydrobromide, 3.0 g) and 1-nitro-2,2-bis-methylthioethylene (1.21 g) in acetonitrile (30 ml) was set aside at room temperature for 3 days. The product was chromatographed on a column of silica gel with elution by ethyl acetate, to give 1-nitro-2-methylthio-2-[2-((3-bromo-2-pyridyl)methylthio)ethylamino]ethylene (1.2 g), m.p. 79°–80° (from ethanol-ether).

(Found: C, 36.3; H, 3.9; N, 11.5% $C_{11}N_{14}BrN_3O_2S_2$ requires: C, 36.3; H, 3.9; N, 11.5%).

(ii) When this methylthio compound (1.3 g) is reacted with 4-methyl-5-[(2-aminoethyl)thiomethyl]imidazole (0.7 g) by the procedure of Example 1(a)(ii), the title compound is produced.

EXAMPLE 2

1-Nitro-2-[2-(2-pyridylmethylthio)ethylamino]-2-[2-((4-methyl-5-imidazolyl)methylthio)ethylamino]ethylene.

(i) A solution of 2-[(2-aminoethyl)thiomethyl]pyridine (5.0 g) and 1-nitro-2,2-bis-methylthioethylene (5.28 g) in ethanol was heated under reflux for 3 hours. Concentration and chromatographic purification of the product on a column of silica gel with elution by isopropyl alcohol-ethylacetate (1:5) gave 1-nitro-2-methylthio-2-[2-(2-pyridylmethylthio)ethylamino]ethylene (2.49 g), m.p. 95.5°–96.5°.

(ii) When this methylthio compound (2.4 g) is reacted with 4-methyl-5-[(2-aminoethyl)thiomethyl]imidazole by the producedure of Example 1(b)(ii), the title compound is produced.

EXAMPLE 3

1-Nitro-2-[2-((3-chloro-2-pyridyl)methylthio)ethylamino]-2-[2-((4-methyl-5-imidazolyl)methylthio)ethylamino]ethylene (i) A solution sodium nitrite (2.38 g) in water (10 ml) was added dropwise to a stirred mixture of 3-amino-2-hydroxy-methylpyridine (4.8 g) in aqueous hydrochloric acid (48% 10 ml) and water (5 ml) at 0°–5° C. This solution of the diazonium salt was added to a hot solution of cuprous chloride (2.5 g) in conc. hydrochloric acid and following cessation of nitrogen evolution the mixture was heated on the steam bath for 0.5 hours, diluted with water and saturated with hydrogen sulphide. Filtration, concentration to low bulk and extraction with chloroform yielded 3-chloro-2-hydroxy-methyl-pyridine (3.7 g), m.p. 42°–44° (from n-pentane). This was dissolved in aqueous hydrobromic acid (48%, 50 ml), cysteamine hydrochloride (3.22 g) added and the solution obtained was heated under reflux for 6 hours. Concentration, followed by recrystallisation from aqueous ethanol afforded 2-[(2-aminoethyl)thiomethyl]-3-chloropyridine dihydrobromide (6.0 g), m.p. 250°.

Reaction of the free base derived from the above dihydrobromide with 1-nitro-2-methylthio-2-[2-((4-methyl-5-imidazolyl)methylthio)ethylamino]ethylene by the procedure of Example 1(a)(ii) yields the title product.

EXAMPLE 4

When in the procedure of Example 1(a)(ii) the following compounds:
2-[(2-aminoethyl)thiomethyl]-3-methylpyridine,
2-[(2-aminoethyl)thiomethyl]-6-methylpyridine,
3-[(2-aminoethyl)thiomethyl]pyridine,
4-[(2-aminoethyl)thiomethyl]pyridine,
2-[(2-aminoethyl)thiomethyl]-3-hydroxypyridine,
2-[(2-aminoethyl)thiomethyl]-5-hydroxypyridine and
2-[(2-aminoethyl)thiomethyl]-3-aminopyridine,
are reacted with 1-nitro-2-methylthio-2-[2-((4-methyl-5-imidazolyl)methylthio)ethylamino]ethylene the products are, respectively:

1-nitro-2-[2-((3-methyl-2-pyridyl)methylthio)ethylamino]-2-[2-((4-methyl-5-imidazolyl)methylthio)ethylamino]ethylene, 1-nitro-2-[2-(6-methyl-2-pyridyl)methylthio)ethylamino]-2-[(4-methyl-5-imidazolyl)methylthio)ethylamino]ethylene, 1-nitro-2-[2-(3-pyridylmethylthio)ethylamino]-2-[2-((4-methyl-5-imidazolyl)methylthio)ethylamino]ethylene, 1-nitro-2-[2-(4-pyridylmethylthio)ethylamino]-2-[2-((4-methyl-5-imidazolyl)methylthio)ethylamino]ethylene, 1-nitro-2-[2-((3-hydroxy-2-pyridyl)methylthio)ethylamino]-2-[2-(4-methyl-5-imidazolyl)methylthio)ethylamino]ethylene, 1-nitro-2-[2-((5-hydroxy-2-pyridyl)methylthio)ethylamino]-2-[(4-methyl-5-imidazolyl)methylthio)ethylamino]ethylene and 1-nitro-2-[2-((3-amino-2-pyridyl)methylthio)ethylamino]-2-[2-((4-methyl-5-imidazolyl)methylthio)ethylamino]ethylene.

EXAMPLE 5

1-Nitro-2-[3-(2-pyridylthio)propylamino]-2-[2-((4-methyl-5-imidazolyl)methylthio)ethylamino]ethylene Reaction of 1-nitro-2-methylthio-2-[2-((4-methyl-5-imidazolyl)methylthio)ethylamino]ethylene with 2-(3-aminopropylthio)pyridine according to the procedure of Example 1(a)(ii) yields the title compound.

EXAMPLE 6

1-Nitro-2-[2-(2-(2-pyridyl)ethylthio)ethylamino]-2-[2-((4-methyl-5-imidazolyl)methylthio)ethylamino]ethylene.

Reaction of 1-nitro-2-methylthio-2-[2-((4-methyl-5-imidazolyl)methylthio)ethylamino]ethylene with 2-[2-(2-aminoethyl)thioethyl]pyridine according to the procedure of Example 1(a)(ii) yields the title compound.

EXAMPLE 7

1-Nitro-2-[4-(2-pyridyl)butylamino]-2-[2-((4-methyl-5-imidazolyl)methylthio)ethylamino]ethylene.

When 2-(4-aminobutyl)pyridine is reacted with 1-nitro-2-methylthio-2-[2-((4-methyl-5-imidazolyl)methylthio)ethylamino]ethylene in the procedure of Example 1(a)(ii), the title compound is produced.

EXAMPLE 8

1-Nitro-2-[2-((3-chloro-2-pyridyl)methylthio)ethylamino]-2-[4-(4-imidazolyl)butylamino]ethylene (i) A solution of 4-(4-aminobutyl)imidazole (from the dihydrobromide (3.6 g) and 1-nitro-2,2-bis-methylthio-ethylene (2.0 g)) in acetonitrile (50 ml) was set aside at room temperature for 3 days. The product was chromatographed on a column of silica gel with elution by ethyl acetate, to give 1-nitro-2-methylthio-2-[4-(4-imidazolyl)butylamino]ethylene.

(ii) Reaction of 2-[(2-aminoethyl)thiomethyl]-3-chloropyridine with this methylthio compound by the procedure of Example 1(a)(ii) yields the title product.

EXAMPLE 9

1-Nitro-2-[2-((3-chloro-2-pyridyl)methylthio)ethylamino]-2-[3-(2-imidazolylthio)propylamino]ethylene.

By the procedure of Example 8 (i), 2-(3-aminopropylthio)imidazole (from the dihydrobromide (3.8 g)) is reacted with 1-nitro-2,2-bis-methylthioethylene (2.0 g) to give 1-nitro-2-methylthio-2-[3-(2-imidazolylthio)-propylamino]ethylene which, on treatment with 2-[(2-aminoethyl)thiomethyl]-3-chloropyridine by the procedure of Example 1(a)(ii) yields the title compound.

EXAMPLE 10

1-Nitro-2-[2-((3-chloro-2-pyridyl)methylthio)ethylamino]-2-[2-(2-(4-imidazolyl)ethylthio)ethylamino]ethylene 4-[2-(2-Aminoethylthio)ethyl]imidazole (from the dihydrobromide (4.0 g) is reacted with 1-nitro-2,2-bis-methylthioethylene (2.0 g) by the procedure of Example 8(i) and the resultant 1-nitro-2-methylthio-2-[2-(2-(4-imidazolyl)ethylthio)ethylamino]ethylene is treated with 2-[(2-aminoethyl)thiomethyl]-3chloropyridine by the procedure of Example 1(a)(ii) to yield the title compound.

EXAMPLE 11

1-Nitro-2-[2-(2-pyridylmethylthio)ethylamino]-2-[2-((4-bromo-5-imidazolyl)methylthio)ethylamino]ethylene When 4-bromo-5-[(2-aminoethyl)thiomethyl]-imidazole (from the dihydrobromide (4.8 g)) is reacted with 1nitro-2,2-bis-methylthioethylene (2.0 g) according to the procedure of Example 8(i) and the resultant 1-nitro-2-methylthio-2-[2-((4-bromo-5-imidazolyl)methylthio)ethylamino]ethylene reacted with 2-[(2-aminoethyl)thiomethyl]pyridine by the procedure of Example 1(a)(ii), the title compound is produced.

EXAMPLE 12

1-Nitro-2-[2-((3-chloro-2-pyridyl)methylthio)ethylamino]-2-[2-((2-amino-4-imidazolyl)methylthio)ethylamino]ethylene Freshly prepared sodium amalgam (90 g) is added over 75 minutes to a stirred solution of serine ethyl ester dihydrochloride (3.0 g) in water/ethanol (2:1), the temperature being maintained within the range of from $-12°$ to $-10°$ and the pH at about 2.5 by the addition of 5N hydrochloric acid. After a further 45 minutes the mixture is allowed to warm to 10° and the precipitated free mercury is removed. Cyanamide is added and the mixture warmed to 50° for 30 minutes, left at 0° for 18 hours and evaporated to dryness. After washing with ether to remove any unchanged cyanamide, the residue is extracted with hot ethanol and heated with hot ethanolic picric acid. Concentration and cooling of the solution gives 2amino-4-hydroxymethylimidazole picrate.

Reaction of 2-amino-4-hydroxymethylimidazole hydrochloride (which is obtained by treating the picrate salt with hydrochloric acid) with cysteamine hydrochloride and reaction of the resulting 2amino-4-[(2-aminoethyl)thiomethyl]imidazole with 1-nitro-2,2-bis-methylthioethylene according to the procedure of Example 8(i) gives 1-nitro-2-methylthio-2-[2-((2-amino-4-imidazolyl)methylthio)ethylamino]ethylene. Finally, reaction with 2-[(2-aminoethyl)thiomethyl]-3-chloropyridine by the procedure of Example 1(a)(ii) produces the title compound.

EXAMPLE 13

When a solution of 1-nitro-2-[2-((3-chloro-2-pyridyl)-methylthio)ethylamino]-2-[2-((4-methyl-5-imidazolyl)-methylthio)ethylamino]ethylene in acetone is treated with ion-exchange resin IRA 400 in the chloride form the corresponding hydrochloride addition salt is formed.

Similarly, by using the above procedure with ion-exchange resin IRA 400 which has been converted to the bromide, iodide and sulphate respectively the hydrobromide, hydriodide and hydrogen sulphate addition salts of 1-nitro-2-[2-((3-chloro-2-pyridyl)methylthio)ethylamino]-2-[2-((4-methyl-5-imidazolyl)-methylthio)ethylamino]ethylene may be produced.

EXAMPLE 14

| Ingredients | Amounts |
| --- | --- |
| 1-Nitro-2-[2-((3-chloro-2-pyridyl)methylthio)-ethylamino]-2-[2-(4-methyl-5-imidazolylmethylthio)-ethylamino]ethylene | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 15

| Ingredients | Amounts |
| --- | --- |
| 1-Nitro-2-[2-((3-bromo-2-pyridyl)methylthio)-ethylamino]-2-[2-((4-methyl-5-imidazolyl)-methylthio)ethylamino]ethylene | 200 mg |
| Lactose | 100 mg |

The ingredients are screened, mixed and filled into a hard gelatin capsule.

EXAMPLE 16

1-Nitro-2-[2-((3-chloro-2-pyridyl)methylthio)ethylamino]-2-[3-(2-oxazolylthio)propylamino]ethylene (i) Hydrochloric acid (90 ml) was added to potassium thiocyanate in ethanol (1.8 l.) with stirring. Following filtration from inorganic material, glycollaldehyde (35.9 g) was added and the resulting solution was heated under reflux for 24 hours. Concentration, followed by cooling afforded a white solid, which following recrystallisation from ethanol afforded oxazole-2-thiol (30 g), m.p. 143°–144°.

(ii) 3-Bromopropylphthalimide (13.4 g) was added to a stirred solution of sodium ethoxide (from 1.15 g sodium) and oxazole-2-thiol (5.1 g) in ethanol (100 ml). The resultant solution was heated under reflux for 2.5 hours and concentrated under reduced pressure. The residue was triturated with water (100 ml) to afford 2-(3-phthalimidopropylthio)oxazole (14 g), m.p. 101°. Recrystallisation from ethanol gave the pure oxazole, m.p. 102°–103°.

(iii) Hydrazine hydride (5.3 g) was added carefully to a solution of 2-(3-phthalimidopropylthio)oxazole (10 g) in ethanol (173 ml) with stirring. The solution was then heated under reflux for 25 minutes. After cooling, and filtration from phthalhydrazide, the filtrate was concentrated under reduced pressure and the residue was re-evaporated with ethanol to yield crude 2-(3-aminopropylthio)oxazole.

(iv) By the procedure of Example 8(i), 2-(3-aminopropylthio)oxazole (2.1 g) is reacted with 1-nitro-2,2-bis-methylthioethylene (2.0 g) to give 1-nitro-2-methylthio-2-[3-(2-oxazolylthio)propylamino]ethylene (2.1 g) which, on reaction with 2-[(2-aminoethyl)thiomethyl]-3-chloropyridine by the procedure of Example 1(a)(ii) gives the title product (2.2 g).

EXAMPLE 17

1-Nitro-2-[2-((3-chloro-2-pyridyl)methylthio)ethylamino]-2-[3-(4-methyl-2-oxazolylthio)-propylamino]ethylene (i) The reaction of 4-methyloxazole-2-thiol (5.8 g) with 3-bromopropylphthalimide (13.4 g) using the conditions described in Example 19 afforded 4-methyl-2-(3-phthalimidopropylthio)oxazole (14 g), m.p. 92°–93° (ethanol-ether).

(ii) Treatment of the phthalimide compound (3.0 g) with hydrazine (1.53 g) followed by reaction of the product directly with 1-nitro-2,2-bis-methylthioethylene (2.2 g) and then with 2-[(2-aminoethyl)thiomethyl]-3-chloropyridine under the conditions described in Example 8 affords the title product.

EXAMPLE 18

1-Nitro-2-[2-((3-chloro-2-pyridyl)methylthio)ethylamino]-2-[2-((4-methyl-5-oxazolyl)methylthioethylamino]ethylene (i) Phthalimidoethanethiol (2 g) was added portionwise with stirring to a solution of sodium ethoxide (prepared from 0.23 g of sodium) in ethanol (20 ml) at 0° under a nitrogen atmosphere. After stirring at 0° for a further 2½ hours, the resulting yellow solution was cooled with an ice-salt bath and a solution of 4-methyl-5-chloromethyloxazole (0.86 g) in ethanol (5 ml) was added dropwise over 10 minutes. After addition the mixture was stirred at room temperature overnight, then acidified with ethanolic hydrogen chloride and evaporated to dryness. Addition of water precipitated unreacted phthalimidoethanethiol (0.6 g) which was removed by filtration. The filtrate was concentrated and basified with aqueous sodium bicarbonate solution to furnish a white precipitate which, on recrystallisation from aqueous ethanol, gave 4-methyl-5-[(2-phthalimidoethyl)thiomethyl]oxazole (0.75 g). A stirred mixture of this phthalimido derivative (0.62 g) in aqueous hydrobromic acid (40 ml 18%) was heated under reflux overnight. After cooling to 0°, the resulting clear solution was filtered and the filtrate evaporated to dryness. Recrystallisation of the residue from ethanol gave 4-methyl-5-[(2-aminoethyl)thiomethyl]oxazole dihydrobromide (0.52 g).

(ii) Reacting 4-methyl-5-[(2-aminoethyl)thiomethyl]oxazole with 1-nitro-2,2-bis-methylthioethylene and then with 2-[(2-aminoethyl)thiomethyl]-3-chloropyridine by the procedure of Example 8 gives the title product.

EXAMPLE 19

Using 5-(2-chloroethyl)-4-methyloxazole as starting material in the procedure of Example 18 the product is 1-nitro-2-[2-((3-chloro-2-pyridyl)methylthio)ethylamino]-2-[2-(2-(4-methyl-5-oxazolyl)ethyl)thioethylamino]ethylene.

Also, using 2-amino-5-(2-chloroethyl)oxazole (prepared by reacting 2-amino-5-(2-hydroxyethyl)oxazole with thionyl chloride) in the procedure of Example 18 gives 1-nitro-2-[2-((3-chloro-2-pyridyl)methylthio)ethylamino]-2-[2-(2-(2-amino-5-oxazolyl)ethyl)thioethylamino]ethylene.

EXAMPLE 20

1-Nitro-2-[2-((3-chloro-2-pyridyl)methylthio)ethylamino]-2-[2-((5-chloro-2-methyl-4-oxazolyl)methylthio)ethylamino]-ethylene Reduction of 5-chloro-2-methyl-4-oxazolecarboxylic acid with diborane to the corresponding 4-hydroxymethyl compound, conversion of this to the 4-chloromethyl compound and use of this chloromethyl compound as the starting material in the procedure of Example 18 gives the title compound.

EXAMPLE 21

| Ingredients | Amounts |
| --- | --- |
| 1-Nitro-2-[2-((3-chloro-2-pyridyl)methylthio)ethylamino]-2-[3-(2-oxazolylthio)propylamino]-ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 22

| Ingredients | Amounts |
| --- | --- |
| 1-Nitro-2-[2-((3-chloro-2-pyridyl)methylthio)ethylamino-2-[3-(4-methyl-2-oxazolylthio)propylamino]ethylene | 200 mg |
| Lactose | 100 mg |

The ingredients are mixed and filled into a hard gelatin capsule.

EXAMPLE 23

1-Nitro-2-[2-((3-chloro-2-pyridyl)methylthio)ethylamino]-2-[2-(3-isoxazolylmethylthio)ethylamino]-ethylene (i) A solution of 3-chloromethylisoxazole (5.8 g) and cysteamine hydrochloride (6.25 g) in aqueous hydrobromic acid (48%, 100 ml) was heated under reflux for 6 hours. Concentration in the presence of water and subsequently n-propanol, followed by recrystallisation of the residue from isopropyl alcohol-ethanol afforded 3-[(2-aminoethyl)thiomethyl]isoxazole hydrobromide, m.p. 131°–133°.

(Found: Br, 33.6; S, 13.7. $C_6H_{10}N_2OS \cdot HBr$ requires: Br, 33.4; S, 13.4).

(ii) by the procedure of Example 8(i), 3-[(2-aminoethyl)thiomethyl]isoxazole (from the hydrobromide (3.7 g)) is reacted with 1-nitro-2,2-bis-methylthioethylene (3.5 g) to give 1-nitro-2-methylthio-2-[2-(3-isoxazolylmethylthio)ethylamino]ethylene (3.6 g) which, on reaction with 2-[(2-aminoethyl)thiomethyl]-3-chloropyridine by the procedure of Example 1(a)(ii) gives the title product (3.5 g).

EXAMPLE 24

Using the following chloromethylisoxazoles (prepared from the corresponding hydroxymethylisoxazoles by treatment thereof with thionyl chloride) as starting materials in the procedure of Example 23:
3-chloromethyl-5-methylisoxazole,
3-bromo-5-chloromethylisoxazole and
4-(2-chloroethyl)-5-methylisoxazole
the products are, respectively:
1-nitro-2-[2-((3-chloro-2-pyridyl)methylthio)ethylamino]-2-[2-(5-methyl-3-isoxazolylmethylthio)ethylamino]ethylene,
1-nitro-2-[2-((3-chloro-2-pyridyl)methylthio)ethylamino]-2-[2-(3-bromo-5-isoxazolylmethylthio)ethylamino]ethylene and
1-nitro-2-[2-((3-chloro-2-pyridyl)methylthio)ethylamino]-2-[2-(2-(5-methyl-4-isoxazolyl)ethylthio)ethylamino]ethylene.

EXAMPLE 25

Using, in the procedure of Example 23, 3-mercaptopropylamine in place of cysteamine, the product is 1- nitro-2-[2-((3-chloro-2-pyridyl)methylthio)ethylamino]-2-[3-(3-isoxazolylmethylthio)propylamino]ethylene.

EXAMPLE 26

| Ingredients | Amounts |
| --- | --- |
| 1-Nitro-2-[2-((3-chloro-2-pyridyl)methylthio)-ethylamino]-2-[2-(3-isoxazolylmethylthio)-ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 27

| Ingredients | Amounts |
| --- | --- |
| 1-Nitro-2-[2-((3-chloro-2-pyridyl)methylthio)-ethylamino]-2-2-(3-isoxazolylmethylthio)-ethylamino]ethylene | 200 mg |
| Lactose | 100 mg |

The ingredients are mixed and filled into a hard gelatin capsule.

EXAMPLE 28

1-Nitro-2-[2-((3-chloro-2-pyridyl)methylthio)ethylamino]-2-[2-(3-(1,2,4-triazolyl)methylthio)ethylamino]ethylene By the procedure of Example 8(i) 3-[(2-aminoethyl)-thiomethyl]-1,2,4-triazole (from the dihydrobromide (2.2g)) is reacted with 1-nitro-2,2-bis-methylthioethylene (1.7 g) to give 1-nitro-2-methylthio-2-[2-(3-(1,2,4-triazolyl)methylthio)-ethylamino]ethylene (1.5 g) which on reaction with 2-[(2-aminoethyl)thiomethyl]-3-chloropyridine by the procedure of Example 1(a)(ii) gives the title product (1.7 g).

EXAMPLE 29

1-Nitro-2-[2-((3-chloro-2-pyridyl)methylthio)ethylamino]-2-[2-(4-methyl-3-(1,2,4-triazolyl)methylthio)ethylamino]ethylene (i) Ethoxyacetyl chloride (57 g) was added slowly to a stirred solution of 4-methylthiosemicarbazide (53.5 g) in dry pyridine (500 ml) at 0°-5°. The mixture was allowed to attain room temperature and stirring was continued for 18 hours. Following concentration under reduced pressure the residue was treated with a solution of sodium (21.4 g) in ethanol (500 ml) and the mixture was heated under reflux for 24 hours. Following concentration and acidification with hydrochloric acid a solid was obtained. After partial concentration the solid was collected and recrystallised from ethyl acetate to give 3-ethoxymethyl-4-methyl-1,2,4-triazoline-5-thione (53 g) m.p. 137°-138°.

The thione (44 g) was desulphurised by slow addition to a solution prepared from nitric acid (75 ml) water (150 ml) and sodium nitrite (1.5 g) at 15°-20°. Following subsequent basification with sodium carbonate and concentration, the residue was extracted with ethanol-ether 1:1 and distilled to afford 3-ethoxymethyl-4-methyl-1,2,4-triazole (30 g) b.p. 154°-156°/0.05 mm. The above compound (15 g) dissolved in 48% aqueous hydrobromic acid (150 ml) was heated under reflux for 24 hours and concentrated to dryness to give a mixture of 4-methyl-3-bromomethyl-1,2,4-triazole and 4-methyl-3-hydroxymethyl-1,2,4-triazole.

(ii) This mixture was reacted directly in solution in aqueous hydrobromic acid with cysteamine hydrochloride by heating under reflux overnight. After cooling, the solution was evaporated to dryness and the residual solid washed with ethanol/ether to give 3-[(2-aminoethyl)thiomethyl]-4-methyl-1,2,4-triazole dihydrobromide, m.p. 175°-177° C.

(iii) Using 3-[(2-aminoethyl)thiomethyl]-4-methyl-1,2,4-triazole (from the dihydrobromide) as the starting material in the procedure of Example 28 yields the title product.

EXAMPLE 30

By the procedure of Example 29 (ii) and (iii), using the following triazoles as starting materials:
3-amino-5-hydroxymethyl-1,2,4-triazole,
3-bromo-5-hydroxymethyl-1,2,4-triazole and
3-(2-chloroethyl)-1,2,4-triazole
the products are, respectively,
1-nitro-2-[2-((3-chloro-2-pyridyl)methylthio)ethylamino]-2-[2-(3-amino-5-(1,2,4-triazolyl)methylthio)ethylamino]ethylene,
1-nitro-2-[2-((3-chloro-2-pyridyl)methylthio)ethylamino]-2-[2-(3-bromo-5-(1,2,4-triazolyl)methylthio)ethylamino]ethylene and
1-nitro-2-[2-((3-chloro-2-pyridyl)methylthio)ethylamino]-2-[2-(2-(3-(1,2,4-triazolyl)ethyl)thio)ethylamino]ethylene.

EXAMPLE 31

1-Nitro-2-[2-((3-chloro-2-pyridyl)methylthio)ethylamino]-2-[2-((5-hydroxy-4-1,2,3-triazolyl)methylthio)ethylamino]ethylene Alkaline hydrolysis of 5-hydroxy-4-carboethoxy-(1,2,3)-triazole to the corresponding carboxylic acid, conversion of the acid to the methyl ester and reduction of this ester with lithium aluminium hydride in tetrahydrofuran gives 5-hydroxy-4-hydroxymethyl-(1,2,3)-triazole. When this compound is used as the starting material in the procedure of Example 29 (ii) and (iii) the title compound is produced.

EXAMPLE 32

1-Nitro-2-[2-((3-chloro-2-pyridyl)methylthio)ethylamino]-2-[4-(3-1,2,4-triazolyl)butylamino]ethylene Use of 3-(4-aminobutyl)-1,2,4-triazole (from the dihydrochloride) as the starting material in the procedure of Example 8(i) and (ii) results in the production of the title compound.

EXAMPLE 33

1-Nitro-2-[2-((3-chloro-2-pyridyl)methylthio)ethylamino]-2-[3-(3-(1,2,4-triazolyl)thio)propylamino]ethylene (i) A solution of 3-mercapto-1,2,4-triazole and 3-aminopropanol in hydrobromic acid is heated under reflux for 24 hours. The reaction mixture is evaporated to dryness and the residue recrystallised from ethanol/ether to give 3-(3-aminopropylthio)-1,2,4-triazole dihydrobromide.

(ii) Conversion of this dihydrobromide to the free base which is then used as the starting material in the procedure of Example 8(i) and 8(ii) yields the title product.

EXAMPLE 34

When a solution of 1-nitro-2-[2-((3-chloro-2-pyridyl)methylthio)ethylamino]-2-[2-(3-(1,2,4-triazolyl)methylthio)ethylamino]ethylene in acetone is treated with ion-exchange resin IRA 400 in the chloride form the corresponding hydrochloride addition salt is formed.

Similarly, by using the above procedure with ion-exchange resin IRA 400 which has been converted to the bromide, iodide and sulphate respectively the hydrobromide, hydriodide and hydrogen sulfate addition salts of 1-nitro-2-[2-((3-chloro-2-pyridyl)methylthio)ethylamino]-2-[3-(3-(1,2,4-triazolyl)methylthio)ethylamino]ethylene may be produced.

EXAMPLE 35

| Ingredients | Amounts |
| --- | --- |
| 1-Nitro-2-[2-((3-chloro-2-pyridyl)methylthio)-ethylamino]-2-[2-(3-(1,2,4-triazolyl)methylthio)-ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 36

| Ingredients | Amounts |
| --- | --- |
| 1-Nitro-2-[2-((3-chloro-2-pyridyl)methylthio)ethylamino-2-[2-(4-methyl-3-(1,2,4-triazolyl)-methylthio)ethylamino]ethylene | 200 mg |
| Lactose | 100 mg |

The ingredients are mixed and filled into a hard gelatin capsule.

EXAMPLE 37

1-Nitro-2-[2-((3-bromo-2-pyridyl)methylthio)ethylamino]-2-[2-(2-thiazolylmethylthio)ethylamino]ethylene (i) By the procedure of Example 8(i), 2-[(2-aminoethyl)thiomethyl]thiazole (from the dihydrobromide, 4.0 g) is reacted with 1-nitro-2,2-bis methylthioethylene (2.0 g) to give 1-nitro-2-methylthio-2-[(2-thiazolylmethylthio)ethylamino]ethylene, m.p. 63°–64°.

(ii) Reaction of 1-nitro-2-methylthio-2-[2-(2-thiazolylmethylthio)ethylamino]ethylene with 2-[(2-aminoethyl)thiomethyl]-3-bromopyridine according to the process of Example 1(a)(ii) yields the title compound.

EXAMPLE 38

1-Nitro-2-[2-((3-bromo-2-pyridyl)methylthio)ethylamino]-2-[2-(4-thiazolylmethylthio)ethylamino]ethylene When 4-[(2-aminoethyl)thiomethyl]thiazole (from the dihydrobromide) is used as the starting material in the procedure of Example 37, the title compound is produced.

EXAMPLE 39

1-Nitro-2-[2-((3-bromo-2-pyridyl)methylthio)ethylamino]-2-[3-(2-thiazolylthio)propylamino]ethylene Using 2-(3-aminopropylthio)thiazole (from the dihydrobromide) as the starting material in the procedure of Example 37 gives the title compound.

EXAMPLE 40

1-Nitro-2-[2-((3-bromo-2-pyridyl)methylthio)ethylamino]-2-[2-(5-thiazolylmethylthio)ethylamino]ethylene When 5-[(2-aminoethyl)thiomethyl]thiazole (from the dihydrobromide) is used as the starting material in the procedure of Example 37 the title compound is produced.

EXAMPLE 41

1-Nitro-2-[2-((3-bromo-2-pyridyl)methylthio)ethylamino]-2-[2-((2-amino-4-thiazolyl)methylthio)ethylamino]ethylene Using 2-amino-4-[(2-aminoethyl)thiomethyl]thiazole as the starting material in the procedure of Example 37 gives the title compound.

EXAMPLE 42

Using the following thiazoles as starting materials in the procedure of Example 29(ii) and 29(iii):
2 hydroxymethyl-4-methylthiazole,
4-chloromethyl-2-methylthiazole,
2-chloro-4-chloromethylthiazole and
4-(2-chloroethyl)thiazole
the products are, respectively:
1-nitro-2-[2-((3-chloro-2-pyridyl)methylthio)ethylamino]-2-[2-((4-methyl-2-thiazolyl)methylthio)ethylamino]ethylene,
1-nitro-2-[2-((3-chloro-2-pyridyl)methylthio)ethylamino]-2-[2-((2-methyl-4-thiazolyl)methylthio)ethylamino]ethylene,
1-nitro-2-[2-((3-chloro-2-pyridyl)methylthio)ethylamino]-2-[2-((2-chloro-4-thiazolyl)methylthio)ethylamino]ethylene and
1-nitro-2-[2-((3-chloro-2-pyridyl)methylthio)ethylamino]-2-[2-(2-(4-thiazolyl)ethyl)thioethylamino]ethylene.

EXAMPLE 43

1-Nitro-2-[2-((3-chloro-2-pyridyl)methylthio)ethylamino]-2-[2-((2-hydroxy-4-thiazolyl)methylthio)ethylamino]ethylene 2-Hydroxy-4-thiazolecarboxylic acid is converted to the methyl ester and the ester is reduced with lithium aluminium hydride in tetrahydrofuran to give 2-hydroxy-4-hydroxymethylthiazole. Using this compound as the starting material in the procedure of Example 29(ii) and 29(iii) gives the title compound.

EXAMPLE 44

1-Nitro-2-[2-((3-bromo-2-pyridyl)methylthio)ethylamino]-2-[4-(2-thiazolyl)butylamino]ethylene Using 2-(4-aminobutyl)thiazole as the starting material in the procedure of Example 37 results in the production of the title compound.

EXAMPLE 45

| Ingredients | Amounts |
| --- | --- |
| 1-Nitro-2-[2-((3-bromo-2-pyridyl)methylthio)-ethylamino]-2-[2-(2-thiazolylmethylthio)-ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 46

| Ingredients | Amounts |
| --- | --- |
| 1-Nitro-2-[2-((3-bromo-2-pyridyl)methylthio)-ethylamino]-2-[2-(2-thiazolylmethylthio)-ethylamino]ethylene | 200 mg |
| Lactose | 100 mg |

The ingredients are mixed and filled into a hard gelatin capsule.

EXAMPLE 47

1-Nitro-2-[2-((3-chloro-2-pyridyl)methylthio)ethylamino]-2-[2-(3-isothiazolylmethylthio)ethylamino]ethylene (i) A solution was prepared by the gradual addition of cysteamine hydrochloride (2.03 g) to sodium (0.83 g) dissolved in ethanol (50 ml) with stirring at 0° under a nitrogen atmosphere. After stirring for 2 hours at 0° 3-bromomethylisothiazole (3.2 g) was added dropwise over 15 minutes at 0°, the reaction mixture subsequently being set aside overnight at room temperature. Following acidification to pH 3.5 with hydrochloric acid, concentration and re-evaporation with ethanol, the residue was dissolved in ethanol, filtered and concentrated to yield 3-[(2-aminoethyl)thiomethyl]isothiazole hydrochloride (3.5 g). This was converted directly to the free base by treatment with aqueous potassium carbonate and extraction with ether. The extracts were dried over magnesium sulphate, dried and concentrated to yield the amine base as an oil (1.56 g).

(ii) By the procedure of Example 8(i), this amine base is reacted with 1-nitro-2-,2-bis-methylthioethylene to give 1-nitro-2-methylthio-2-[2-(3-isothiazolylmethylthio)ethylamino]ethylene m.p. 64.5°–65.5°. Reaction of this compound with 2-[(2-aminoethyl)thiomethyl]-3-chloropyridine in the procedure of Example 1(a)(ii) yields the title compound.

EXAMPLE 48

1-Nitro-2-[2-((3-chloro-2-pyridyl)methylthio)ethylamino]-2-[2-((4-bromo-3-isothiazolyl)methylthio)ethylamino]ethylene (i) The reaction of 4-bromo-3-(bromomethyl)isothiazole (8.5 g) with cysteamine (from cysteamine hydrochloride (3.76 g) was performed under conditions similar to those described in Example 47. From the reaction there was obtained 4-bromo-3-[(2-aminoethyl)thiomethyl]isothiazole hydrobromide, which, following recrystallisation from ethanol-ether and acetonitrile, gave needles (4.05 g) m.p. 111°–112°. The amine base (2.73 g) was isolated by basification with sodium hydroxide and extraction with chloroform.

(ii) Use of the amine base as the starting material in the procedure of Example 47(ii) gives the title compound.

EXAMPLE 49

Using the following halomethylisothiazoles as starting materials in the procedure of Example 47:
3-bromomethyl-4-chloroisothiazole and
4-bromo-5-chloromethyl-3-methylisothiazole
the products are, respectively:
1-nitro-2-[2-((3-chloro-2-pyridyl)methylthio)ethylamino]-2-[2-((4-chloro-3-isothiazolyl)methylthio)ethylamino]ethylene and
1-nitro-2-[2-((3-chloro-2-pyridyl)methylthio)ethylamino]-2-[2-((4-bromo-3-methyl-5-isothiazolyl)methylthio)ethylamino]ethylene.

EXAMPLE 50

1-Nitro-2-[2-((3-chloro-2-pyridyl)methylthio)ethylamino]-2-[2-((3-methyl-4-isothiazolyl)methylthio)ethylamino]ethylene Reacting 4-hydroxymethyl-3-methylisothiazole (3.0 g) with cysteamine hydrochloride (2.8 g) in 48% aqueous hydrobromic acid (50 ml) by the procedure of Example 29(ii) gives 3-methyl-4-[(2-aminoethyl)thiomethyl]isothiazole hydrobromide. The base is obtained by basifying with aqueous potassium carbonate, extracting with chloroform, drying the extracts over magnesium sulphate and concentrating. Using the amine (5.0 g) as the starting material in the procedure of Example 47(ii) yields the title compound.

EXAMPLE 51

1-Nitro-2-[2-((3-chloro-2-pyridyl)methylthio)ethylamino]-2-[2-(2-(3-isothiazolyl)ethyl)thioethylamino]ethylene 3-Isothiazoleacetic acid is converted to the methyl ester and the ester is reduced with lithium aluminium hydride in tetrahydrofuran to give 3-(2-hydroxyethyl)isothiazole. Reacting this hydroxyethyl compound with thionyl chloride gives 3-(2-chloroethyl)isothiazole. Using 3-(2-chloroethyl)isothiazole in the procedure of Example 47(i) and (ii) gives the title compound.

EXAMPLE 52

1-Nitro-2-[2-((3-chloro-2-pyridyl)methylthio)ethylamino]-2-[3-(3-isothiazolylmethylthio)propylamino]ethylene When in the procedure of Example 47, cysteamine hydrochloride is replaced by 3-mercaptopropylamine hydrochloride, the title compound is produced.

EXAMPLE 53

| Ingredients | Amounts |
| --- | --- |
| 1-Nitro-2-[2-((3-chloro-2-pyridyl)methylthio)-ethylamino]-2-[2-(3-isothiazolylmethylthio)-ethylamino]ethylene | 150 mg |
| Sucrose | 75 mg |
| Starch | 25 mg |
| Talc | 5 mg |
| Stearic acid | 2 mg |

The ingredients are mixed and filled into a hard gelatin capsule.

EXAMPLE 54

| Ingredients | Amounts |
| --- | --- |
| 1-Nitro-2-[2-((3-chloro-2-pyridyl)methylthio)-ethylamino]-2-[2-((4-bromo-3-isothiazolyl)-methylthio)ethylamino]ethylene | 200 mg |
| Lactose | 100 mg |

The ingredients are mixed and filled into a hard gelatin capsule.

EXAMPLE 55

1-Nitro-2-[2-((3-chloro-2-pyridyl)methylthio)ethylamino]-2-[2-((2-amino-5-1,3,4-thiadiazolyl)methylthio)ethylamino]ethylene (i) By the procedure of Example 8(i), 2-amino-5-(2-aminoethyl)thiomethyl-1,3,4-thiadiazole (from the dihydrobromide) is reacted with 1-nitro-2-,2-bis-methylthioethylene to give 1-nitro-2-methylthio-2-[2-((2-amino-5-1,3,4-thiadiazolyl)methylthio)ethylamino]ethylene.

(ii) Reaction of this compound with 2-[(2-aminoethyl)thiomethyl]-3-chlorpyridine according to the process of Example 1(a)(ii) gives the title compound.

EXAMPLE 56

Addition of phosphonyl chloride to a mixture of thiosemicarbazide and methoxyacetic acid at 60°–95° and working up of the product yields 5-amino-2-methoxymethyl-(1,3,4)-thiadiazole, m.p. 177°–179° (from water). When this compound is diazotised and treated with cuprous bromide 5-bromo-2-methoxymethyl-(1,3,4)-thiadiazole results and reaction of this bromo compound with zinc dust in acetic acid at room temperature yields 2-methoxymethyl-(1,3,4)-thiadiazole, m.p. 30.5°–32°.

Using the following thiadiazoles as starting materials in the procedure of Example 29(ii) and 29(iii):
5-chloro-3-chloromethyl-1,2,4-thiadiazole and
2-methoxymethyl-1,3,4-thiadiazole,
the products are, respectively:
1-nitro-2-[2-((3-chloro-2-pyridyl)methylthio)ethylamino]-2-[2-((5-chloro-3-1,2,4-thiadiazolyl)methylthio)ethylamino]ethylene and
1-nitro-2-[2-((3-chloro-2-pyridyl)methylthio)ethylamino]-2-[2-((2-1,3,4-thiadiazolyl)methylthio)ethylamino]ethylene.

EXAMPLE 57

1-Nitro-2-[2-((3-1,2,5-thiadiazolyl)methylthio)ethylamino]-2-[2-((3-chloro-2-pyridyl)methylthio)ethylamino]ethylene Reaction of 3-methyl-1,2,5-thiadiazole with N-bromosuccinimide results in the production of 3-bromomethyl-1,2,5-thiadiazole.

When 3-bromomethyl-1,2,5-thiadiazole is used as the starting material in the procedure of Example 29(ii) and 29(iii), the title compound is obtained.

EXAMPLE 58

1-Nitro-2-[2-((3-chloro-2-pyridyl)methylthio)ethylamino]-2-[2-(2-(2-amino-5-1,3,4-thiadiazolyl)ethylthio)ethylamino]ethylene 2-Amino-5-(1,3,4-thiadiazole)acetic acid is esterified with anhydrous ethanolic hydrogen chloride and the resulting ethyl ester is reduced with lithium aluminium hydride in tetrahydrofuran to give 2-amino-5-(2-hydroxyethyl)-1,3,4-thiadiazole. Treating this hydroxyethyl compound with thionyl chloride gives 2-amino-5-(2-chloroethyl)-1,3,4-thiadiazole.

Using 2-amino-5-(2-chloroethyl)-1,3,4-thiadiazole as the starting material in the procedure of Example 29(ii) and 29(iii) gives the title compound.

EXAMPLE 59

1-Nitro-2-[2-((3-chloro-2-pyridyl)methylthio)ethylamino]-2-[3-(2-amino-5-(1,3,4-thiadiazolyl)thio)-propylamino]ethylene Using 2-amino-5-(3-aminopropylthio)-1,3,4-thiadiazole (from the dihydrobromide) as the starting material in the procedure of Example 8(i) and (ii) gives the title compound.

EXAMPLE 60

When a solution of 1-nitro-2-[2-((3-chloro-2-pyridyl)methylthio)ethylamino]-2-[2-((2-amino-5-1,3,4-thiadiazolyl)methylthio)ethylamino]ethylene in acetone is treated with ion-exchange resin IRA 400 in the chloride form the corresponding hydrochloride addition salt is formed.

Similarly, by using the above procedure with ion-exchange resin IRA 400 which has been converted to the bromide, iodide and sulphate respectively the hydrobromide, hydriodide and hydrogen sulphate addition salts of 1-nitro-2-[2-((3-chloro-2-pyridyl)methylthio)ethylamino]-2-[2-((2-amino-5-1,3,4-thiadiazolyl)methylthio)ethylamino]ethylene may be produced.

EXAMPLE 61

| Ingredients | Amounts |
| --- | --- |
| 1-Nitro-2-[2-((3-chloro-2-pyridyl)methylthio)-ethylamino]-2-[2-((2-amino-5-1,3,4-thiadiazolyl)-methylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 62

| Ingredients | Amounts |
| --- | --- |
| 1-Nitro-2-[2-((3-chloro-2-pyridyl)methylthio)-ethylamino]-2-[3-((2-amino-5-1,3,4-thiadiazolyl)-thio)propylamino]ethylene | 200 mg |
| Lactose | 100 mg |

The ingredients are mixed and filled into a hard gelatin capsule.

EXAMPLE 63

(i) Reaction of malononitrile with carbon disulphide in the presence of alcoholic sodium methoxide and treatment of the product with methyl iodide (see Berichte, 1962, 95, 2861) yields 1,1-dicyano-2,2-bis-methylthioethylene.

(ii) Reaction of 2-[(2-aminoethyl)thiomethyl]-3-chloropyridine with 1,1-dicyano-2,2-bis-methylthioethylene by the procedure of Example 1(b)(i) yields 1,1-dicyano-2-methylthio-2-[2-((3-chloro-2-pyridyl)methylthio)ethylamino]ethylene.

(iii) Reaction of this methylthio compound in the procedure of Example 1(b)(ii) with the following amines:
  5-[(2-aminoethyl)thiomethyl]-4-methylimidazole,
  2-(3-aminopropyl)thiooxazole,
  3-[(2-aminoethyl)thiomethyl]isoxazole,
  3-[(2-aminoethyl)thiomethyl]-1,2,4-triazole,
  2-[(2-aminoethyl)thiomethyl]thiazole,
  3-[(2-aminoethyl)thiomethyl]isothiazole and
  2-amino-5-[(2-aminoethyl)thiomethyl]-1,3,4-thiadiazole
yields the following compounds:
  1,1-dicyano-2-[2-((3-chloro-2-pyridyl)methylthio)ethylamino]-2-[2-((4-methyl-5-imidazolyl)methylthio)ethylamino]ethylene,
  1,1-dicyano-2-[2-((3-chloro-2-pyridyl)methylthio)ethylamino]-2-[3-(2-oxazolylthio)propylamino]ethylene,
  1,1-dicyano-2-[2-((3-chloro-2-pyridyl)methylthio)ethylamino]-2-[2-(3-isoxazolylmethylthio)ethylamino]ethylene,
  1,1-dicyano-2-[2-((3-chloro-2-pyridyl)methylthio)ethylamino]-2-[2-(3-(1,2,4-triazolyl)methylthio)ethylamino]ethylene,
  1,1-dicyano-2-[2-((3-chloro-2-pyridyl)methylthio)ethylamino]-2-[2-(2-thiazolylmethylthio)ethylamino]ethylene,
  1,1-dicyano-2-[2-((3-chloro-2-pyridyl)methylthio)ethylamino]-2-[2-(3-isothiazolylmethylthio)ethylamino]ethylene and
  1,1-dicyano-2-[2-((3-chloro-2-pyridyl)methylthio)ethylamino]-2-[2-((2-amino-5-(1,3,4-thiazolyl)methylthio)ethylamino]ethylene.

EXAMPLE 64

(i) Reaction of 1-cyano-2,2-bis-methoxyethylene (J.A.C.S., 1949, 71, 47) with 2-[(2-aminoethyl)thiomethyl]-3-chloropyridine by the procedure of Example 1(b)(i) yields 1-cyano-2-methoxy-2-[2-((3-chloro-2-pyridyl)methylthio)ethylamino]ethylene.

(iii) Reaction of this methoxy compound in the procedure of Example 1(b)(ii) with the following amines:
  5-[(2-aminoethyl)thiomethyl]-4-methylimidazole,
  2-(3-aminopropyl)thiooxazole,
  3-[(2-aminoethyl)thiomethyl]isoxazole,
  3-[(2-aminoethyl)thiomethyl]-1,2,4-triazole,
  2-[(2-aminoethyl)thiomethyl]thiazole,
  3-[(2-aminoethyl)thiomethyl]isothiazole and
  2-amino-5-[(2-aminoethyl)thiomethyl]-1,3,4-thiadiazole,
yields the following compounds:
  1-cyano-2-[2-((3-chloro-2-pyridyl)methylthio)ethylamino]-2-[2-((4-methyl-5-imidazolyl)methylthio)ethylamino]ethylene,
  1-cyano-2-[2-((3-chloro-2-pyridyl)methylthio)ethylamino]-2-[3-(2-oxazolylthio)propylamino]ethylene,
  1-cyano-2-[2-((3-chloro-2-pyridyl)methylthio)ethylamino]-2-[2-(3-isoxazolylmethylthio)ethylamino]ethylene,
  1-cyano-2-[2-((3-chloro-2-pyridyl)methylthio)ethylamino]-2-[2-(3-(1,2,4-triazolyl)methylthio)ethylamino]ethylene,
  1-cyano-2-[2-((3-chloro-2-pyridyl)methylthio)ethylamino]-2-[2-(2-thiazolylmethylthio)ethylamino]ethylene,
  1-cyano-2-[2-((3-chloro-2-pyridyl)methylthio)ethylamino]-2-[2-(3-isothiazolylmethylthio)ethylamino]ethylene and
  1-cyano-2-[2-((3-chloro-2-pyridyl)methylthio)ethylamino]-2-[2-((2-amino-5-(1,3,4-thiadiazolyl)methylthio)ethylamino]ethylene.

EXAMPLE 65

(i) Reaction of methylphenylsulphone with carbon disulphide under strongly basic conditions and treatment of the product with methyliodide yields 1-benzenesulphonyl-2,2-bis-methylthio ethylene.

(ii) Reaction of 2-[(2-aminoethyl)thiomethyl]-3-chloropyridine with 1-benzenesulphonyl-2,2-bis-methylthioethylene by the procedure of Example 1(b)(i) yields 1-benzenesulphonyl-2-methylthio-2-[2-((3-chloro-2-pyridyl)methylthio)ethylamino]ethylene.

(iii) When this methylthio compound is reacted in the procedure of Example 1(b)(ii) with the following amines:
  5-[(2-aminoethyl)thiomethyl]-4-methylimidazole,
  2-(3-aminopropyl)thiooxazole,
  3-[(2-aminoethyl)thiomethyl]isoxazole,
  3-[(2-aminoethyl)thiomethyl]-1,2,4-triazole,
  2-[(2-aminoethyl)thiomethyl]thiazole,
  3-[(2-aminoethyl)thiomethyl]isothiazole and
  2-amino-5-[(2-aminoethyl)thiomethyl]-1,3,4-thiadiazole,
the following compounds are produced:
  1-benzenesulphonyl-2-[2-((3-chloro-2-pyridyl)methylthio)ethylamino]-2-[2-((4-methyl-5-imidazolyl)methylthio)ethylamino]ethylene,
  1-benzenesulphonyl-2-[2-((3-chloro-2-pyridyl)methylthio)ethylamino]-2-[3-(2-oxazolylthio)propylamino]ethylene,
  1-benzenesulphonyl-2-[2-((3-chloro-2-pyridyl)methylthio)ethylamino]-2-[2-(3-isoxazolylmethylthio)ethylamino]ethylene,
  1-benzenesulphonyl-2-[2-((3-chloro-2-pyridyl)methylthio)ethylamino]-2-[2-(3-(1,2,4-triazolyl)methylthio)ethylamino]ethylene,
  1-benzenesulphonyl-2-[2-((3-chloro-2-pyridyl)methylthio)ethylamino]-2-[2-(2-thiazolylmethylthio)ethylamino]ethylene,
  1-benzenesulphonyl-2-[2-((3-chloro-2-pyridyl)methylthio)ethylamino]-2-[2-(3-isothiazoly-(methylthio)ethylamino]ethylene and
  1-benzenesulphonyl-2-[2-((3-chloro-2-pyridyl)methylthio)ethylamino]-2-[2-((2-amino-5-(1,3,4-thiadiazolyl)methylthio)ethylamino]ethylene.

EXAMPLE 66

When, in place of methylphenylsulphone, the following sulphones are used as the starting materials in Example 65:
  methyl-(4-chlorphenyl)sulphone,
  methyl-(3,4-dichlorophenyl)sulphone and
  methyl-(4-methylphenyl)sulphone
the corresponding 1-substitutedphenyl-2-[2-((3-chloro-2-pyridyl)methylthio)ethylamino]-2-[(heterocyclic or heterocyclicalkyl)thio)alkylamino]ethylene compounds are produced.

EXAMPLE 67

(i) Reaction of phenylsulphonylacetonitrile with carbon disulphide in the presence of sodium hydride and treatment of the product with methyl iodide yields 1-benzenesulphonyl-1-cyano-2,2-bis-methylthioethylene.

(ii) Reaction of 1-benzenesulphonyl-1-cyano-2,2-bis-methylthioethylene by the procedure of Example 1(b)(ii) with the following amines:

5-[(2-aminoethyl)thiomethyl]-4-methylimidazole,
2-(3-aminopropyl)thiooxazole,
3-[(2-aminoethyl)thiomethyl]isoxazole,
3-[(2-aminoethyl)thiomethyl]-1,2,4-triazole,
2-[(2-aminoethyl)thiomethyl]thiazole,
3-[(2-aminoethyl)thiomethyl]isothiazole and
2-amino-5-[(2-aminoethyl)thiomethyl]-1,3,4-thiadiazole, yields the following compounds:

1-benzenesulphonyl-1-cyano-2-[2-((3-chloro-2-pyridyl)methylthio)ethylamino]-2-[2-((4-methyl-5-imidazolyl)methylthio)ethylamino]ethylene, 1-benzenesulphonyl-1-cyano-2-[2-((3-chloro-2-pyridyl)methylthio)ethylamino]-2-[3-(2-oxazolylthio)propylamino]ethylene, 1-benzenesulphonyl-1-cyano-2-[2-((3-chloro-2-pyridyl)methylthio)ethylamino]-2-[2-(3-isoxazolylmethylthio)ethylamino]ethylene, 1-benzenesulphonyl-1-cyano-2-[2-((3-chloro-2-pyridyl)methylthio)ethylamino]-2-[2-(3-(1,2,4-triazolyl)methylthio)ethylamino]ethylene, 1-benzenesulphonyl-1-cyano-2-[2-((3-chloro-2-pyridyl)methylthio)ethylamino]-2-[2-(2-thiazolylmethylthio)ethylamino]ethylene, 1-benzenesulphonyl-1-cyano-2-[2-((3-chloro-2-pyridyl)methylthio)ethylamino]-2-[2-(3-isothiazolylmethylthio)ethylamino]ethylene and 1-benzenesulphonyl-1-cyano-2-[2-((3-chloro-2-pyridyl)methylthio)ethylamino]-2-[2-((2-amino-5-(1,3,4-thiadiazolyl)methylthio)ethylamino]ethylene.

We claim:

1. A compound of the formula:

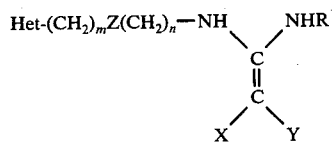

wherein X and Y, which may be the same or different, are hydrogen, nitro, cyano or $SO_2Ar$ but are not both hydrogen; or both nitro R is $Het'(CH_2)_{m_1}Z'(CH_2)_{n_1}$; Z and $Z'$ are sulphur or methylene; $m$ and $m_1$ are 0, 1 or 2 and $n$ and $n_1$ are 2 or 3, provided that each of the sum of $m$ and $n$ and the sum of $m_1$ and $n_1$ is 3 or 4; Het is a pyridine ring which ring is optionally substituted by lower alkyl, hydroxyl, halogen or amino; Het' is a nitrogen containing 5 membered heterocyclic ring selected from thiazole, isothiazole or thiadiazole which ring is optionally substituted by lower alkyl, hydroxyl, halogen or amino; and Ar is phenyl optionally substituted by halogen or methyl, or a pharmaceutically acceptable acid addition salt thereof.

2. A compound of claim 1 wherein X and Y are hydrogen, nitro or cyano but are not both hydrogen or both nitro.

3. A compound of claim 1 wherein R is $Het'CH_2SCH_2CH_2$, Z is sulphur, $m$ is 1 and $n$ is 2.

4. A compound of claim 1 wherein Het' is thiazole or isothiazole and is optionally substituted by methyl, hydroxyl, halogen or amino.

5. A compound of claim 1 wherein X is nitro and Y is hydrogen.

6. A compound of claim 1, said compound being 1-nitro-2-[2-(2-thiazolylmethylthio)ethylamino]-2-[2-((3-chloro-2-pyridyl)methylthio)ethylamino]ethylene.

7. A compound of claim 1 wherein one of X and Y is nitro, cyano or $SO_2Ar$ and the other is hydrogen or one of X and Y is cyano and the other is cyano or $SO_2Ar$.

8. A pharmaceutical composition to inhibit H-2 histamine receptors comprising a pharmaceutical carrier and, in an effective amount to inhibit said receptors, a compound of claim 1.

9. A method of inhibiting H-2 histamine receptors which comprises administering orally or parenterally to an animal in need thereof, in an effective amount to inhibit said receptors, a compound of claim 1.

* * * * *

UNITED STATES PATENT AND TRADEMARK OFFICE
CERTIFICATE OF CORRECTION

PATENT NO. : 4,080,459

DATED : March 21, 1978

INVENTOR(S) : Graham John Durant, John Colin Emmett, Charon Robin Ganellin and Hunter Douglas Prain It is certified that error appears in the above-identified patent and that said Letters Patent are hereby corrected as shown below:

Column 2, line 21, below the structural formula, insert -- FORMULA I -- .

Column 24, line 11, "hydrogen; or both nitro R" should read -- hydrogen or both nitro; R -- .

Signed and Sealed this

Eighth Day of August 1978

[SEAL]

Attest:

RUTH C. MASON
*Attesting Officer*

DONALD W. BANNER
*Commissioner of Patents and Trademarks*